(12) United States Patent
Raabe et al.

(10) Patent No.: US 7,570,987 B2
(45) Date of Patent: Aug. 4, 2009

(54) PERSPECTIVE REGISTRATION AND VISUALIZATION OF INTERNAL AREAS OF THE BODY

(75) Inventors: Andreas Raabe, Bad Homburg (DE); Niels Frielinghaus, Heimstetten (DE); Jens Witte, München (DE)

(73) Assignee: BrainLAB AG, Feldkirchen (DE)

( * ) Notice: Subject to any disclaimer, the term of this patent is extended or adjusted under 35 U.S.C. 154(b) by 773 days.

(21) Appl. No.: 10/815,226

(22) Filed: Mar. 30, 2004

(65) Prior Publication Data
US 2005/0010099 A1 Jan. 13, 2005

Related U.S. Application Data

(60) Provisional application No. 60/489,753, filed on Jul. 24, 2003.

(51) Int. Cl.
*A61B 5/05* (2006.01)
(52) U.S. Cl. .......................... 600/426; 600/414
(58) Field of Classification Search ................. 600/414
See application file for complete search history.

(56) References Cited

U.S. PATENT DOCUMENTS

| 5,961,456 | A |   | 10/1999 | Gildenberg |         |
|-----------|---|---|---------|------------|---------|
| 6,006,126 | A | * | 12/1999 | Cosman     | 600/426 |

2002/0087062 A1   7/2002  Schmidt et al.

FOREIGN PATENT DOCUMENTS

| DE | 39 31 531   | 4/1990  |
| DE | 198 07 884  | 9/1999  |
| DE | 100 15 824  | 10/2001 |
| DE | 101 51 438  | 1/2003  |
| EP | 1 208 808   | 5/2002  |

OTHER PUBLICATIONS

Liao et al. Intra-operative Real-Time 3-D Information Display System Based on Integral Videography. MICCAI 2001, LNCS 2208, pp. 392-400, 2001.*
Peters. Image-guided Surgery and Therapy: Current Status and Future Directions. Proceedings of SPIE vol. 4319 (2001).*

* cited by examiner

*Primary Examiner*—Eric F Winakur
*Assistant Examiner*—Michael T Rozanski
(74) *Attorney, Agent, or Firm*—Renner, Otto, Boisselle & Sklar, LLP

(57) ABSTRACT

The invention relates to a method for registering an image data set for visualizing internal areas of the body. The method can include determining the relative position of an imaging device and of an external body part associated with an internal area of the body and producing an image data set for the internal area of the body by means of the imaging device. The spatial position of the external body part is determined and the image data of the internal area of the body are registered or assigned according to relative position, with respect to the spatial position of the external body part, on the basis of the relative positional information.

18 Claims, 4 Drawing Sheets

PERSPECTIVE REGISTRATION AND VISUALIZATION OF INTERNAL AREAS OF THE BODY

RELATED APPLICATION DATA

This application claims priority of U.S. Provisional Application No. 60/489,753, filed on Jul. 24, 2003, which is incorporated herein by reference in its entirety.

FIELD OF THE INVENTION

The invention relates to the registration and visualization of internal areas of the body, body structures and organs within the framework of technically assisting medical treatments. In particular, it relates to the perspective, spatial representation of three-dimensional data sets, objects or surface models in image-assisted surgery, i.e., the utilization of anatomical, three-dimensional volume data sets of the human body that do not contain surface points of the patient's body for registering, and which it has therefore not hitherto been possible to use for navigation.

BACKGROUND OF THE INVENTION

Surgical treatment with the aid of image-assisted navigation systems, also called tracking systems, is known in principle. Such a system is, for example, described in DE 196 39 615 C2 and the associated U.S. Pat. No. 6,351,659 B1. Other surgical navigation systems are known, for example, from U.S. Pat. Nos. 4,722,065, 4,791,934 and 5,383,454. Based on data from imaging methods, such as computer tomography, nuclear spin tomography and x-ray transillumination, a number of navigation systems and/or tracking systems use the captured recordings of body parts for a visual and absolute spatial representation of surgical instruments in relation to body parts, such as tissues or bones. In order to ensure the spatial representation of surgical instruments with respect to the patient inside the operating theatre, the coordinate system of the diagnostic data, for example, a computer tomograph, which is fixed by the imaging unit/scanner, has to be aligned with and superimposed onto a second coordinate system assigned to the patient in his actual position in the operating theater. Assigning or aligning the appropriate body structures in the image data set to the patient's actual position in the operating theatre is commonly referred to as registering.

Such registering is usually achieved by a superimposing method, with the aid of anatomical landmarks or special marking points or markers. The data set points are assigned to the real points by means of "paired point matching" or by surface matching between the patient's anatomy and 3D surfaces of the data set. The points existing in the data set are aligned with corresponding points of the patient, i.e., artificial or natural surface points. Once the coordinate systems have been aligned, i.e., once the patient has been registered, the position of a surgical instrument, localized in the patient coordinate system by means of an optical, magnetic or ultrasound-based localization system, can also be represented spatially on the computer screen, positionally exact in the coordinate system of the diagnostic data set, and used to assist in the treatment.

The known methods are based on such co-registration of image data set (CT/MRT) points and patient points, points within the image data set or space being used as absolute reference points. During registration, these absolute reference points are aligned with identical points, which can be identified on the "surface" of the patient.

Disadvantageously, such registration methods cannot be applied in cases in which the image data set only comprises an internal area of the body or only parts of the anatomy (for example, only vessels). One problem is that these internal areas of the body often do not comprise any natural landmarks (for example, in the patient's brain) and also cannot easily be provided with artificial landmarks. Therefore, these volume data sets cannot be registered using the conventional methods. They are, however, important in, among other areas, vascular surgery in which high-resolution image data sets indicate an exactly defined, internal body volume in which the vascular disease (for example, an aneurysm) and the exact vascular paths are situated. Previously, such visualizations from image data sets for internal areas of the body have only been used separately as a source of information of the operating surgeon, i.e., the information available form them was, for example, viewed by the physician beforehand, but remained unused as far as the patient present in the operating theatre was concerned.

SUMMARY OF THE INVENTION

One object of the present invention to provide a method for registering an image data set for the visualization of internal areas of the body. In accordance with one aspect, an image data set for an internal area of the body can be registered at least in as much as that it is made possible to visually represent the information from the image data set, such that they are aligned, assigned to the patient actually situated in the operating theatre, and of use to the surgeon.

In accordance with one aspect of the invention, the invention is directed to a method for registering an image data set for the visualization of internal areas of the body. The method can include determining the relative position of an imaging device and of an external body part assigned to an internal area of the body and producing an image data set for the internal area of the body by means of the imaging device. The method can include determining the spatial position of the external body part and registering, or assigning according to relative position, the image data of the internal area of the body with respect to the spatial position of the external body part, on the basis of the relative positional information.

In other words, an external body part can be used to form a bridge by means of which registration of the internal area of the body is then enabled. To this end, relative positional information is obtained by determining a relative positional relationship between the external body part and the imaging device. This relative positional information can then be used to at least determine the alignment of the internal area of the body in the real operating theatre and to correspondingly represent the appropriate image data set visually. Such a method could also be called "perspective registration" or as a whole "perspective navigation". Such perspective registration or navigation makes it possible to obtain alignment information for real internal areas of the body and corresponding areas in the image data set without having to use artificial or natural landmarks.

Applications include, among other things, vascular surgery, as well as any surgery in which an exact working direction and/or the direction to the target but not an exact distance are required (for example, aneurysm surgery, angioma surgery, aligning screw connections, drill channels, etc.). Here, the exact spatial position of the instrument and the patient's anatomy is not particularly important, but rather the exact, current spatial orientation with respect to the viewing direction and/or working direction of the surgeon. Thus, the present invention makes three-dimensional data sets of internal areas of the body of use to image-assisted surgery.

In one embodiment of the present invention, the relative position of the imaging device and of the external body part is determined in a coordinate system that is fixed with respect to the imaging device.

In accordance with another embodiment, the step of determining the relative position of the imaging device and of the external body part includes providing the external body part with markings, moving the imaging device from its initial position into one or more positions in which the markings appear in a defined position with respect to each other, and recording the movement of the imaging device.

The markings can be attached to the external body part in such a way that they appear, in one viewing direction, in a linear arrangement, or covering each other. This viewing direction can then be reproduced and clearly determined.

Furthermore, it is possible to determine the spatial position of the external body part by means of the markings of or on the external body part, using a medical tracking system. The markings that are used to determine the relative position with respect to the imaging device can thus advantageously also exhibit a second function, which then comes into effect when an absolute position in the operating theatre is to be determined. In the present case, this absolute position is the spatial position of the external body part.

If, as mentioned above, the movement of the imaging device is recorded and/or stored for determining the relative position, this can be achieved on the basis of at least two angles which define at least two positions which are different from each other, in which the markings appear in a defined position with respect to each other. This defined position can, for example, be a linear arrangement. In accordance with one embodiment, the image data can be represented visually from the direction from which an observer looks onto the internal area of the body. In general, the viewing direction of the observer can also be determined here by means of a medical tracking system. In addition, there exists the possibility of representing the image data visually from the direction of an instrument, such as a microscope, pointed at the internal area of the body. The alignment of the instrument, too, can be determined by means of a medical tracking system. If a surgical microscope is used, the image data can advantageously be superimposed in an image inter-reflecting unit.

The invention can be applied when the image data set is a high-resolution volume image data set of an internal area of the body, such as a high-resolution x-ray image data set, for example, a rotational angiography image data set. Furthermore, the present invention can find advantage when the image data are converted to a three-dimensional representation of structures, such as vascular structures, of the internal area of the body, which can then be represented visually.

Using relative positional information (angles) and perspective registration, the invention allows a volume data set to be aligned without points of the surface of the patient having to be contained in the image data set. Once registered, the data set is represented exactly in perspective and allows a working direction and projection to be exactly navigated. The image data set is not captured in an absolute coordinate system, but rather in a relative 360° space. Each view of the data set is, for example, defined by two angular dimensions, and absolute points in the three-dimensional coordinate system are not required. Registration is independent of absolute points, since the relative position of the captured image data set with respect to the patient is detected and the image data set is then harmonized with the relative position of the patient during registration. Accordingly, a surgeon can then also orientate himself on the basis of the visualized image data set, since its represented alignment corresponds to his viewing direction or to the direction of his instrument, and he can thus obtain information from the visualization of the image data set which is not available to him by looking at the actual patient. He can, for example, fix vascular paths beforehand and allow for these paths in his operation.

BRIEF DESCRIPTION OF THE DRAWINGS

These and further features of the present invention will be apparent with reference to the following description and drawings, wherein.

The invention will now be explained in more detail on the basis of examples and an embodiment. In the enclosed drawings, there is shown.

DETAILED DESCRIPTION OF THE INVENTION

Figure 1:
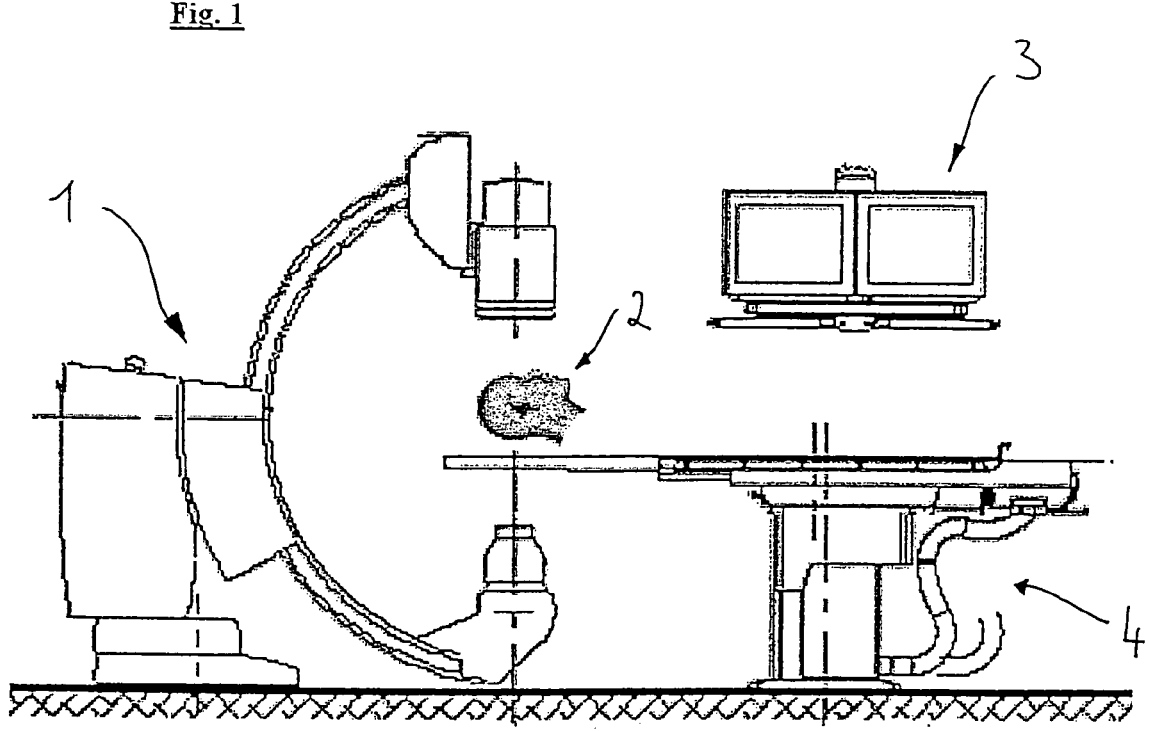
FIG. 1 is a schematic representation of a rotational angiography arrangement.

FIG. 1 shows an imaging device, such as a rotational angiography scanner 1, which can take recordings of a patient, of whom only the head 2 is shown and who lies on an adjustable couch 4. Monitors 3, for example for visually representing anatomic structures, can also be provided in the operating theater. The vascular structure 10 shown, for example, in FIG. 2 lies in the patient's head 2, as can be seen in FIG. 3. The representation in FIG. 2 corresponds to one such as can be obtained as a three-dimensional representation from a volume data set, when the vessels are highlighted and the surrounding structure is faded out. This is mostly enabled by using a contrast medium for angiography recordings and corresponding calculations (computer graphics). The volume data set including the vascular structure 10 is outwardly limited such that it does not contain any external points, i.e., any points on the "surface" of the patient. It is a high-resolution volume data set in order to be able to make the fine vascular structures visible.

Figure 4:
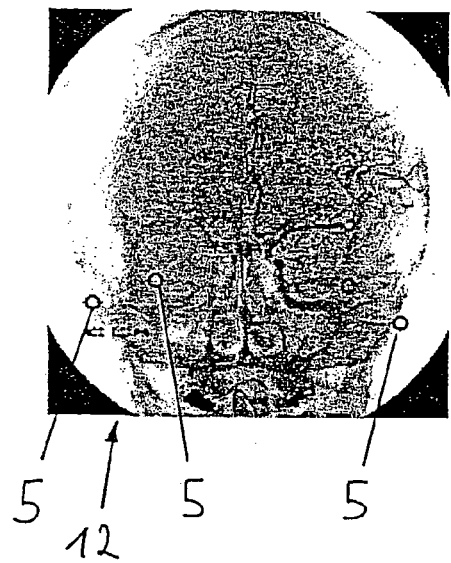
FIG. 4 is an exemplary anterior-posterior angiography recording including marker images, before alignment.
Figure 5:
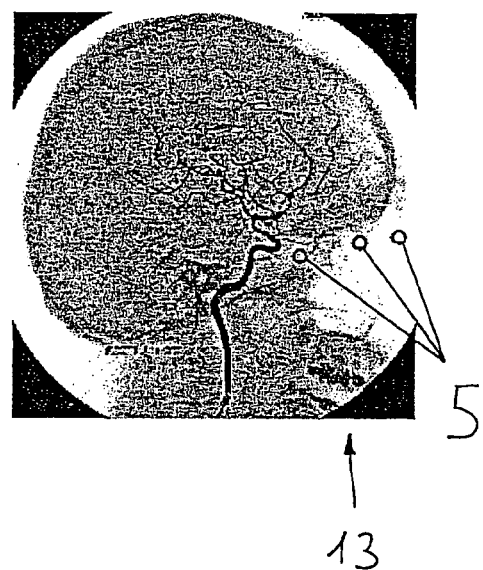
FIG. 5 is an exemplary lateral recording including markers, before alignment.
Figure 6:
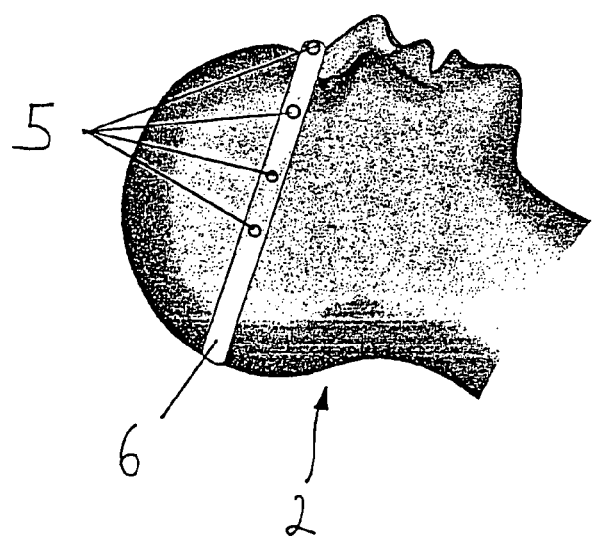
FIG. 6 is a side view of a patient's head including an attached marker localization device.

Two angiography recordings, offset at right angles to each other, such as can be taken in the zero position (FIG. 1) of the scanner 1, are shown in FIGS. 4 and 5. FIG. 4 shows an anterior-posterior recording and FIG. 5 shows a lateral left-right recording. As shown in FIG. 6, for the recording, a localization device 6 including attached markers 5 can be positioned on the patient's head 2 at about brow height. In the zero position of the scanner 1, shown in FIG. 1, the recordings 12 from FIG. 4 and 13 from FIG. 5 therefore show marker images which are not arranged linearly, although they are aligned on the localization device 6 in a line.

Figure 7:
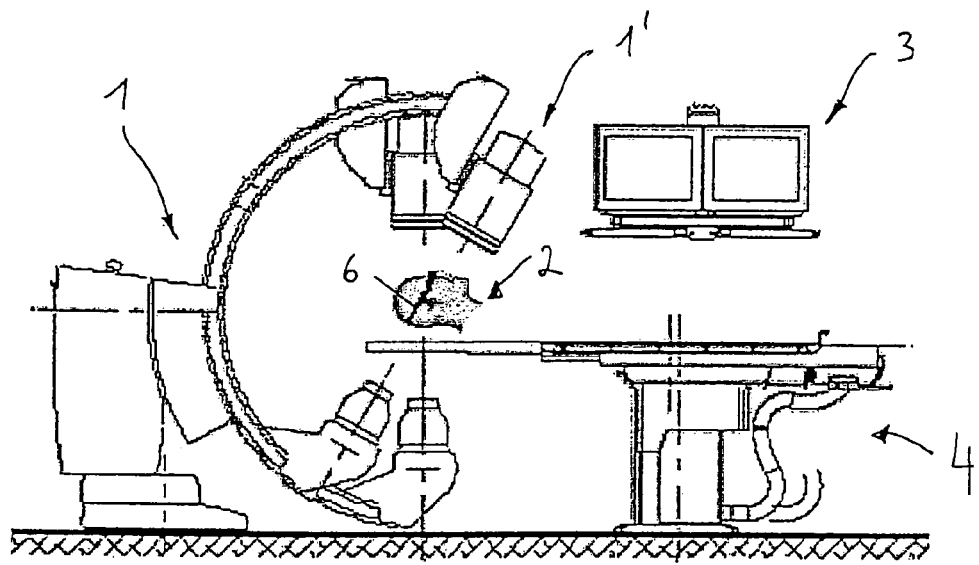
FIG. 7 is a schematic representation of a rotational angiography arrangement in a zero position and in a rotated position of the scanner.
Figure 9:
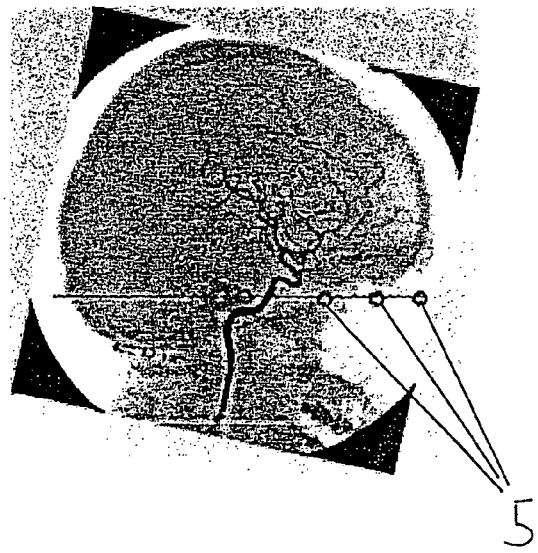
FIG. 9 is an exemplary lateral recording, after alignment.
Figure 10:
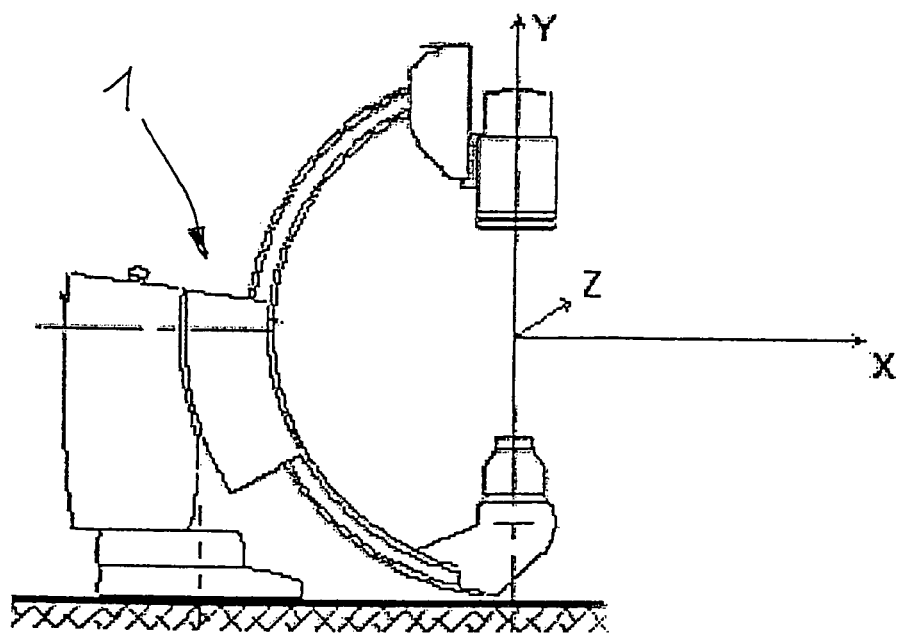
FIGS. 10 and 11 are schematic representations of a scanner in a zero position and in a rotated position, with angles indicated.
Figure 11:
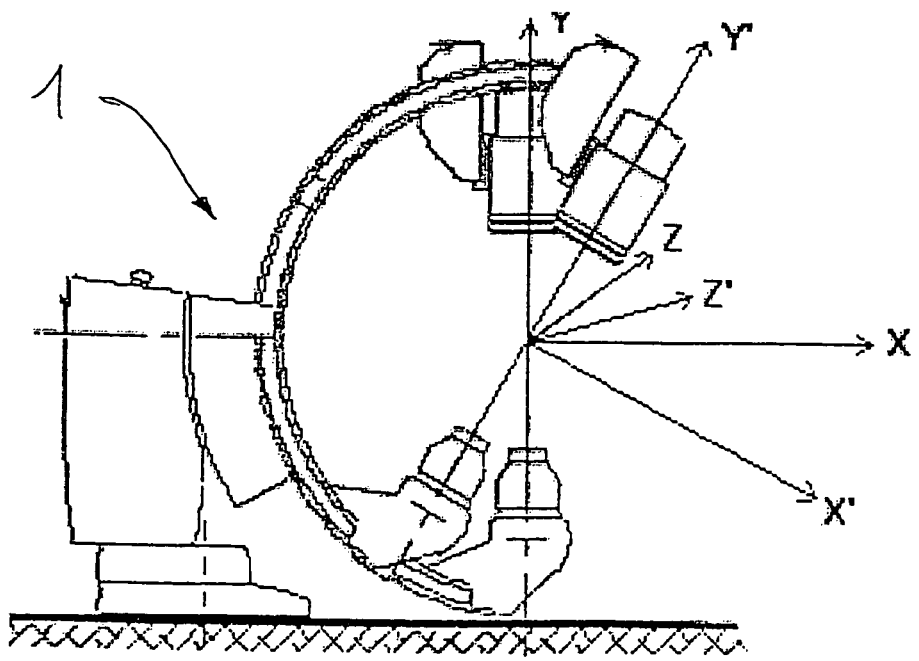

FIG. 7 shows the scanner 1 in the rotational angiography arrangement in two positions, namely once in the zero position and once in a shifted position indicated by 1'. The recording from FIG. 8 was taken in the position shown in FIG. 7, while the recording in FIG. 9 was taken in a position of the scanner rotated by 90° relative to this. As shown, the markers 5 appear in a linear alignment in both recordings, because of the angular rotation. FIGS. 10 and 11 again show the zero position (FIG. 10) and a rotated position (FIG. 11) which in general follows from a rotation from the co-ordinate system X, Y, Z to the co-ordinate system X', Y', Z'.

An example embodiment of the invention will now be explained in more detail. It may also be noted in general that the features of the invention mentioned in this description can also be adapted in any combination.

Figure 2:
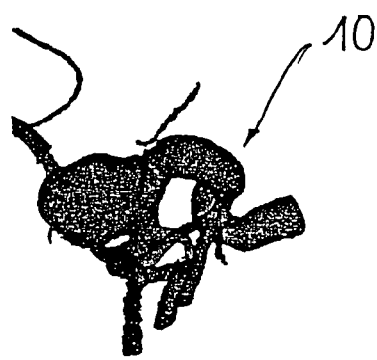
FIG. 2 is a perspective view of an exemplary vascular structure which is represented by means of a three-dimensional volume image data set.
Figure 3:
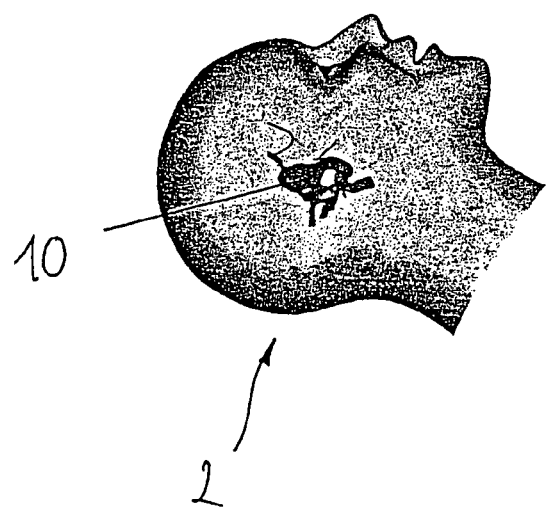
FIG. 3 illustrates the position of the vascular structure shown in FIG. 2 in a patient's head.

In one embodiment, a visualization of a vascular structure 10, shown in FIG. 2, can be made available to the operating physician, always such that he sees it in correct alignment with respect to his current viewing direction and/or the direction of an instrument being used by him, for example, a microscope. The physician can then directly utilize the information, accessible from the 3D volume data set via the structure 10, in order, for example, to better plan the subsequent course of the operation, since in such a case, he already knows how the path of the structure beyond his current open incision continues. Particularly in vascular surgery, in which vascular injuries are absolutely to be avoided, such a technical operating aid is greatly advantageous.

To this end, however, the volume data set 10 first has to be aligned, which is possible if it is registered. The problem here is that the volume data set 10 does not comprise any external patient landmarks or artificial landmarks, and a registration method in accordance with the invention is explained in the following.

The 3D volume data set 10 from the rotational angiography shows only a small tissue structure which is not accessible from outside for the purpose of registration. In accordance with the present embodiment of the invention, a predefined angular coordinate system is therefore used, for example, on the rotational angiography scanner 1, in order to ascertain the spatial position of the structure 10 in the three-dimensional volume data set.

Figure 8:
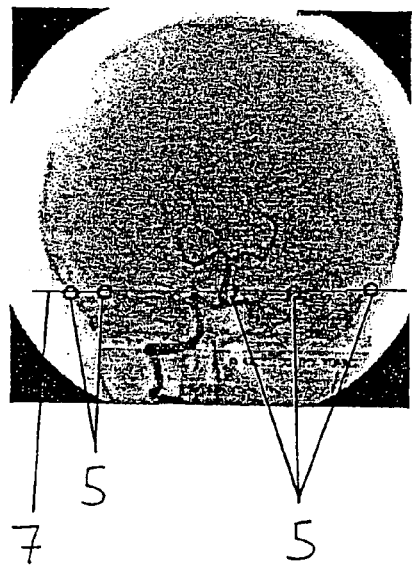
FIG. 8 is an exemplary anterior-posterior recording, after alignment.

To this end, the current position of the patient in the rotational angiography scanner is first ascertained by means of the localization device 6, with respect to the coordinate system of the scanner. As shown in FIG. 7, the scanner 1 is aligned such that the localization device is distinguishable in an exactly fixed, vertical and horizontal alignment, in each of a lateral sample recording (an x-ray image from right to left, FIG. 9) and an anterior-posterior recording (FIG. 8). This is the case if the markers 5 are situated on a line which in FIG. 8, for example, is provided with the reference numeral 7. The angles set for this purpose on the rotational angiography scanner 1 are recorded. This adjustment of the scanner 1 may be seen in FIGS. 10 and 11. In principle, such an adjustment can take place on three co-ordinate axes, leading from the axes X, Y, Z to the axes X', Y', Z'. In one embodiment, it is sufficient to establish and store or record two angles, namely with respect to the lateral recording and with respect to the anterior-posterior recording. What is important is that the change in angle is established and can be recorded, stored, etc. in any way.

Following this, a rotational angiography image data set is produced with the scanner in an arbitrary angular position, specifically a high-resolution data set which only comprises the internal area of the body around the vascular structure 10. This image data set is converted into a 3D volume data set showing the vessels (FIG. 2), with the volume data set being aligned on the scanner angular coordinate system as it is produced.

With the aid of the noted or recorded angle of the positional recording (the recording in the angularly altered position), the rotational angiography volume data set can then be aligned such as it corresponded to the position of the head 2 (the external body part) during rotational angiography. If a tracking device (not shown) is then used in the operating theater, which can ascertain the current position of the patient's head 2 as an absolute position in space on the basis of the markings 5, the position of the patient plane/patient co-ordinate system is thus known, and a relationship between the coordinate system of the 3D volume data set 10 (the scanner co-ordinate system) and the patient co-ordinate system can be established. The zero position can either be known in the tracking system or established. In other words, by using the same points (localization points of the localization device on the patient's head), which were used in the positional recording (angularly rotated scanner), the rotational angiography volume data set 10 can be harmonized with the current position of the patient's head 2.

When an instrument localized by a tracking system, for example an operating microscope (not shown), is then pointed at the patient, the 3D volume can, with the aid of the directional information of the instrument, be spatially and perspectively aligned correctly, corresponding to the optical axis of the microscope (i.e., the viewing direction of the surgeon). It is sufficient here to establish just the directional information of the instrument; it is not necessary to know the exact three-dimensional positional information of the instrument, since it is sufficient for a physician to be viewing the volume data set in the correct alignment, in order to establish how the subsequent vascular structures, in reality still obscured, run. The exact spatial position of the instrument and the patient's anatomy is not particularly important, but rather the exact current spatial alignment of the vessel to be operated on, with respect to the surgeon's viewing direction.

If a surgical microscope is used, the aligned volume data set can be superimposed in an image inter-reflecting unit of the microscope. However, it can also be made available to the physician on a display, for example a screen next to the microscope, or on a virtual reality display.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for registering an image data set for visualizing internal areas of the body, said method comprising:
   determining a relative position of (i) an imaging device, and (ii) an external body part associated with an internal area of the body by:
   providing the external body part with markings;
   moving the imaging device from an initial position into one or more positions in which the markings appear in a defined position with respect to each other; and
   recording the movement of the imaging device;
   producing an image data set for the internal area of the body using the imaging device, wherein the image data set does not include data on the external body part;
   determining a spatial position of the external body part; and
   registering or assigning the image data of the internal area of the body with respect to the spatial position of the external body based on the relative position between the imaging device and the external body part.

2. The method as set forth in claim 1, wherein the relative positions of the imaging device and the external body part are determined in a coordinate system (X, Y, Z) which is fixed with respect to the imaging device.

3. The method as set forth in claim 1, wherein the markings are attached to the external body part such that they appear in one viewing direction in a linear arrangement.

4. The method as set forth in claim 1, wherein the markings are attached to the external body part such that they appear in one viewing direction to be covering each other.

5. The method as set forth in claim 1, wherein the spatial position of the external body part is determined by means of the markings of the external body part using a medical tracking system.

6. The method as set forth in claim 1, wherein the movement of the imaging device is recorded on the basis of at least two angles which define at least two positions which are different from each other, in which the markings appear in a defined position with respect to each other.

7. The method as set forth in claim 1, wherein the image data set is represented visually from a viewing direction from which an observer looks onto the internal area of the body.

8. The method as set forth in claim 7, wherein the viewing direction of the observer is determined by means of a medical tracking system.

9. The method as set forth in claim 1, wherein the image data is represented visually from a direction of an instrument pointed at the internal area of the body.

10. The method as set forth in claim 9, wherein the instrument is a microscope.

11. The method as set forth in claim 9, wherein the image data is superimposed in an image inter-reflecting unit of a surgical microscope.

12. The method as set forth in claim 11, wherein the alignment of the instrument is determined by means of a medical tracking system.

13. The method as set forth in claim 1, wherein the image data set is a high-resolution volume image data set of an internal area of the body.

14. The method as set forth in claim 13, wherein the image data set is a high-resolution x-ray image data set.

15. The method as set forth in claim 14, wherein the image data set is a rotational angiography image data set.

16. The method as set forth in claim 1, wherein the image data is converted to a three-dimensional representation of structures of the internal area of the body, which are then represented visually.

17. The method as set forth in claim 16, wherein the structures are vascular structures.

18. A method for registering an image data set for visualizing an internal area of a body, the method comprising:
   receiving data indicative of a relative position between an imaging device and an external body part, the external body part being associated with an internal area of the body, wherein the data indicative of the relative position includes data representative of the imaging device being in an initial position and one or more other positions in which markers disposed on the external body part appear in a defined position with respect to each other;
   receiving data indicative of an image data set for the internal area of the body, the data being obtained from the imaging device and not including data on the external body part;
   determining a spatial position of the external body part;
   registering or assigning the image data set of the internal area of the body with respect to the spatial position of the external body part based on the relative position between the imaging device and the external body part; and
   displaying an image of the internal area of the body.

* * * * *